United States Patent [19]

Larsen et al.

[11] 4,135,131

[45] Jan. 16, 1979

[54] MICROWAVE TIME DELAY SPECTROSCOPIC METHODS AND APPARATUS FOR REMOTE INTERROGATION OF BIOLOGICAL TARGETS

[75] Inventors: Lawrence E. Larsen, Silver Spring; John H. Jacobi, Bowie, both of Md.

[73] Assignee: The United States of America as represented by the Secretary of the Army, Washington, D.C.

[21] Appl. No.: 842,137

[22] Filed: Oct. 14, 1977

[51] Int. Cl.² .......................................... G01R 27/04
[52] U.S. Cl. ............................... 324/58.5 A; 128/2 A
[58] Field of Search ............ 324/58.5 A, 57 SS, 58 A; 195/103.5 R; 128/2 A, 2 R, 2 S

[56] References Cited

U.S. PATENT DOCUMENTS

| | | | |
|---|---|---|---|
| 3,432,752 | 3/1969 | Frederickson et al. | 324/57 SS |
| 3,441,843 | 4/1969 | Wainwright | 324/57 SS |
| 3,445,762 | 5/1969 | Wu | 324/57 SS |
| 3,586,969 | 6/1971 | Rudisill, Jr. | 324/57 SS |
| 3,956,695 | 5/1976 | Stamm | 324/58.5 A |

Primary Examiner—Stanley T. Krawczewicz
Attorney, Agent, or Firm—William G. Gapcynski; Werten F. W. Bellamy

[57] ABSTRACT

Remote interrogation of biological targets is accomplished in accordance with the present invention by method and apparatus wherein a microwave signal is generated which varies in frequency from a first frequency to a second frequency in a predetermined time period. The signal is divided into two signals, one of which is propagated through a test channel comprising a transmitting antenna for transmitting the signal through the target, and a receiving antenna for receiving the signal transmitted through the target, and the other of which is propagated through a reference channel providing a fixed time delay of propagation. The propagated signals are detected and mixed to produce a time delay spectrum wherein the frequency of each spectral line represents the instantaneous difference in the frequencies of the detected signals.

7 Claims, 5 Drawing Figures

MICROWAVE TIME DELAY SPECTROSCOPIC METHODS AND APPARATUS FOR REMOTE INTERROGATION OF BIOLOGICAL TARGETS

FIELD OF THE INVENTION

The present invention relates generally to spectroscopy methods and apparatus, and more particularly to microwave time delay spectroscopy methods and apparatus for remote interrogation of biological targets.

DESCRIPTION OF THE PRIOR ART AND PRIOR ART STATEMENT

The essential requirements for a microwave measurement technique which is to be used to interrogate remote targets are that it be non-ambiguous for biologically relevant electrical path lengths, and that it be capable of discriminating between biologically relevant path length variations. Further, in order to have practical utility, the measurement technique should be easy to implement, and the data provided thereby must be readily interpretable.

When electromagnetic energy in the microwave region propagates through a biological target, the phase velocity and absorption thereof are a function of the permittivity, or dielectric constant, of the medium. Since the dielectric constant of a biological medium is a function of the composition and functional state of the tissue, the measurement of the total time delay and attenuation in microwave energy propagated through a biological target can theoretically be used to characterize the type, functional state, and thickness of the tissue through which the wave length travels. This capability is to be contrasted with the capability of X-ray interrogation techniques, where it is not possible to characterize tissue types by propagation time measurements. However, any time delay measurement technique which is utilized must provide unambiguous information between multiple paths whose differential propagation time is quite small.

For a number of reasons, localization and characterization of the dielectric properties of nonhomogeneous biological targets cannot be easily accomplished using only single frequency continuous wave (CW) measurements of reflection and transmission coefficients. One important reason is that the energy reaching the receiving antenna cannot be assumed to have followed a single ray path, and the multiple paths of the incident radiation to the receiver preclude simple assumptions about association of a transmission or reflection measurement with a single line integral. Also, a single frequency CW measurement is not capable of discriminating between tissue paths, the electrical length of which differ by more than one wavelength.

Other approaches which have been considered include pulsed radio frequency time delay and group delay measurement techniques. These approaches also suffer from several deficiencies. Pulse techniques require pulses with very fast rise time (100 picoseconds or less) in order to obtain adequate resolution. Such pulses require extremely broadband modulators, amplifiers, transmission lines, and detectors, which are complex and expensive. Group delay techniques are limited in the resolution which is obtainable by the noise and drift present in the network analyzers which must be utilized.

The present invention utilizes a time delay spectrum which is produced by linearly sweeping a microwave signal generator in frequency from a first frequency to a second frequency in a particular period. The generator output is divided into first and second signals which are propagated through a reference channel and a test channel, respectively, and the propagated signals are combined to produce a frequency spectrum which is representative of the differential time delay in the propagation of the signals through their respective channels.

A search of the prior art conducted in connection with the preparation of the present application developed the following patents in which a frequency varying signal and/or the combination of two signals are utilized in a measurement technique: U.S. Pat. No. 3,107,329 (McSkimin); U.S. Pat. No. 3,439,266 (Rogers); U.S. Pat. No. 3,851,244 (Mounce); U.S. Pat. No. Re. 29,008 (Ott). The McSkimin patent is an example of an application of pulse techniques and discloses a method wherein synchronism between two radio frequency pulses, one of which has been transmitted through a test channel, and one of which has been transitted through a reference channel, can be determined by comparison of the more centrally positioned portions of the pulses, so as to avoid the need for wide band apparatus and a high degree of resolution of each individual pulse. In accordance with one embodiment of the McSkimin method, the radio frequency of the pulses is continuously varied while the time interval between the pulses is varied until the signal produced by combining the pulses is at a substantially constant and clean maximum.

The Rogers patent discloses a heterodyne system for testing frequency sensitive electrical devices for insertion loss, return loss, and the like. The system is adapted to test devices which operate over a band of frequencies by the provision of a swept frequency generator which is coupled to a network having two transmission branches. One of the branches includes the device to be tested and the other branch includes an element which renders it electrically long with respect to the other branch. The outputs of the two transmission devices are heterodyned in a mixer to produce an intermediate frequency signal, which has an envelope indicative of a predetermined transmission characteristic of the device.

The Mounce patent discloses a microwave system of the heterodyne type for measuring moisture in sheet materials such as paper, wherein a detector is subjected both to strong signals from a frequency modulated source and to delayed and attenuated signals which have passed twice through the moisture containing material. The reason for doing so is that the strong signal acts as a local oscillator on the detector and forces it out of its high-impedance, high-noise, square-law region into a low-impedance, low-noise, linear region of operation.

The Ott patent discloses a machine for identification of persons wherein the frequency response characteristics of a portion of a person's body to sonic wave energy are compared with previously stored data for the person. Detector means are provided to detect the phase and amplitude of the signal transmitted through the person's body, and correlator means are provided to produce a transfer function representing an algebraic-trigonometric statement of the output divided by the input. In one embodiment a swept frequency source is employed and the output thereof may be applied to the correlator means for comparison with the signal transmitted through the person's body to obtain a transfer function having improved accuracy.

Applicants are also aware of U.S. Pat. No. 3,466,653 (Heyser), which discloses a time delay spectrometer for measuring the audio spectral response of an object which is located in an environment containing radiation reflecting bodies. In the Heyser device, a sound energy source is driven by a sweep frequency oscillator and the output of a sound detector is filtered by a tunable bandpass filter which is tuned or driven so as to follow the frequency of the sweep frequency oscillator by a delay equal to the time required for sound to travel a direct path from the source to the object and then to the detector. The filter thus passes only sound waves following the direct path and rejects sound waves which arrive at a later time when the filter has passed on to a new frequency. Heyser has also worked on ultrasonic imaging systems in which transmission variations through a target are measured. This work has been described in an article by Heyser and Le Croissette, 1 *Ultrasound in Medicine and Biology* 119–131.

Finally, applicants are aware of "CHIRP" radar techniques, wherein swept frequency radar signals are employed to reduce the peak power requirements of the radiated signal, and the delay time of the reflected signals is measured to determine target range. Reference is made to an article by Klauder, et al., appearing in Volume XXXIX of the *Bell System Technical Journal* (1960), at pages 745–808, for a discussion of CHIRP radar techniques.

The prior art cited hereinabove includes, in the opinion of the applicants, the closest prior art of which they are aware. However, there is no representation that no better art exists.

SUMMARY OF THE INVENTION

Remote interrogation of biological targets is accomplished in accordance with the present invention by time delay spectroscopy method and apparatus wherein a microwave signal is generated which varies in frequency from a first frequency to a second frequency in a predetermined time period. The signal is divided into two signals, one of which is propagated through a test channel comprising a transmitting antenna for transmitting the signal through the target, and a receiving antenna for receiving the signal transmitted through the target, and the other of which is propagated through a reference channel providing a fixed time delay of propagation. The propagated signals are detected and mixed to produce a time delay spectrum wherein the frequency of each spectral line represents the instantaneous difference in the frequencies of the detected signals. Preferably, the transmitting and receiving antennas and the target are immersed in water or other high dielectric medium.

In accordance with a further aspect of the invention the time delay spectrum is analyzed to determine the direct ray path through the target by selecting the spectral line having the highest amplitude at the lowest frequency.

Other features and advantages of the invention will be set forth in, or apparent from, the detailed description of a preferred embodiment found hereinbelow.

BRIEF DESCRIPTION OF THE DRAWINGS

FIG. 2b is a side elevational view, of the antenna shown in FIG. 2a.

DETAILED DESCRIPTION OF THE PREFERRED EMBODIMENTS

Figure 1:
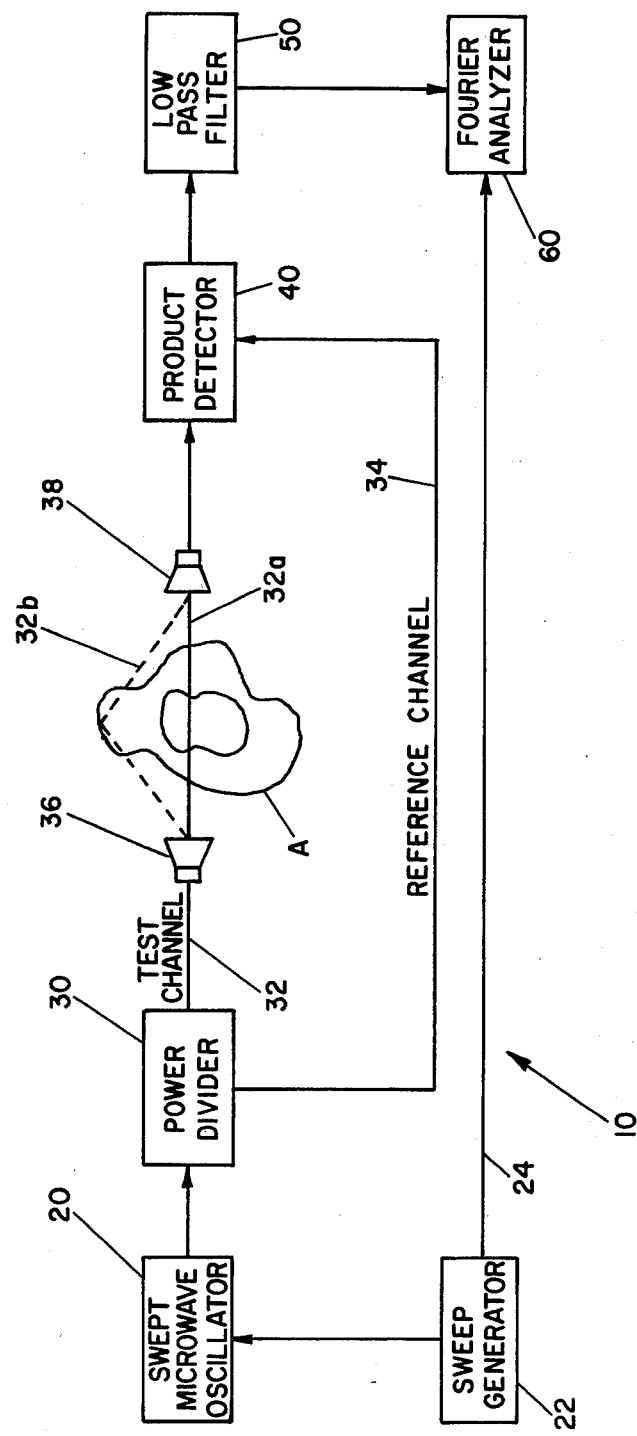
FIG. 1 is a simplified block diagram of a time delay spectrometry system constructed in accordance with the present invention for remote interrogation of a biological target.

Referring to FIG. 1, a system 10 constructed according to the present invention for remote interrogation of a biological target comprises a swept microwave oscillator 20 which is linearly swept by a sweep generator 22 to produce a microwave signal which continuously varies in frequency from a first frequency $f_1$ to a second frequency $f_2$ in a predetermined time period $T_S$.

System 10 further comprises a power divider 30 for dividing the output of oscillator 20 into first and second propagation signals which are propagated, respectively, through a test channel 32 and a reference channel 34. Test channel 32 comprises a transmitting antenna 36, a biological target A situated in free space, generally denoted 37, and a receiving antenna 38. Reference channel 34 provides a signal path having a fixed time delay.

Preferably, the biological target A, as well as antennas 36 and 38, are immersed in water, or other high dielectric constant environment. There are several advantages to a water environment with respect to remote interrogation of a biological target. First, the wavelength of the propagated signal is contracted, which improves the spatial resolution of the line scan. Second, coupling of energy into the target is improved. Third, discrimination of multipaths through the target is facilitated. Fourth, water has acceptable loss, inertness, and tissue match characteristics for biological targets.

System 10 also comprises a product detector 40 for detecting and multiplying, or mixing, the first and second propagation signals following propagation thereof through the corresponding channels 32 and 34 to produce signals representing the time delay spectrum. In the case of sinusoids, the result of the mixing is sinusoids whose frequencies are the sum and difference, respectively, of the frequencies of the input signals. A low pass filter 50 and Fourier analyzer 60 are provided for processing of the time delay spectrum. Filter 50 rejects the spectrum signal whose frequency is the sum of the frequencies of the inputs to detector 40, and also acts as an anti-aliasing filter to reduce errors in the digital Fourier transform produced by analyzer 60. Analyzer 60 digitizes the output of filter 50 and transforms the data to amplitude and phase information in the frequency domain.

Figure 2A:
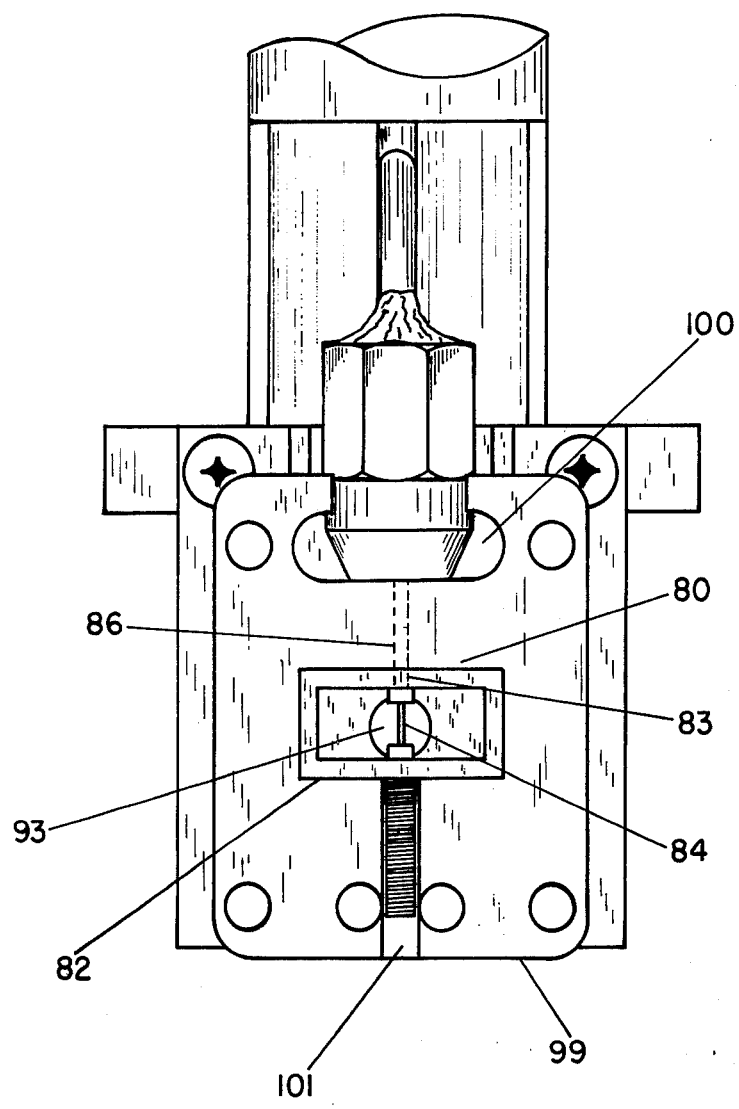
FIG. 2a is a front elevational view, partially cut away, of a perferred antenna embodiment for use in the system of FIG. 1.
Figure 2B:
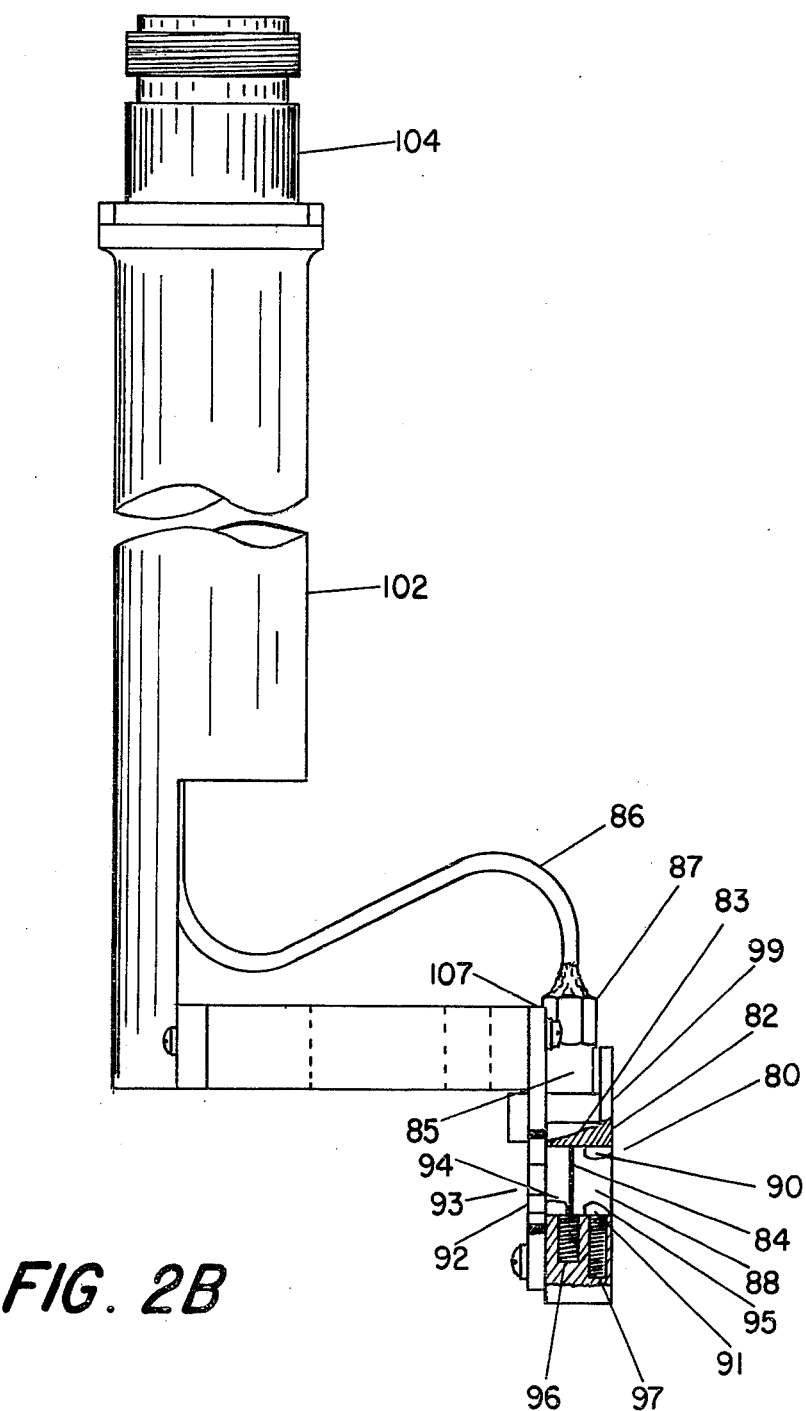

Antennas 36 and 38 should preferably have as large a bandwidth, and as small an aperture, as possible, with a phase center that does not move with frequency. The need for a large bandwidth is a consequence of the swept frequency nature of the interrogating radiation. For a particular measurement, the bandwidth required is determined by the resolution needed, the sweep rates available in oscillator 20, the sweep range available, and the sampling rates provided by the analyzer 60 which is utilized. A small aperture is desirable since if the aperture is too large compared to the area of the dielectric discontinuity being studied, it is not possible for the discontinuity to occlude the direct ray path between antennas 36 and 38, and a condition equivalent to multipath occurs which obscures the desired result. A constant phase center is preferred since movement of the phase center with frequency is equivalent to varying the separation between antennas, which has the effect of broadening the spectral lines in the time delay spectrum. A preferred antenna construction is depicted in FIGS. 2a-2b. The antenna, generally denoted 80, comprises a double ridged waveguide 82, which is approximately 6.7 mm in length. The length of waveguide 82 represents a compromise between internal loss and ease of impedance matching, since a shorter length, on the order of 3 mm, would be preferable from the standpoint of power loss, but would not permit the use of tuning screws for impedance matching.

The top wall of waveguide 82 is provided with an aperture 83, through which the feed probe 84 of a standard 50 ohm impedance coaxial input cable 86 having a fluorocarbon dielectric such as "Teflon" is inserted by means of a standard female connector 85 mounted on the top surface of waveguide 82 and a standard male connector 87 mounted on the end of cable 86.

As shown, the top ridge 90 of waveguide 82 extends longitudinally along the upper interior surface only from the front end of waveguide 82 to the perimeter of aperture 83, while the bottom ridge 91 extends longitudinally along the entire lower interior surface from the front end to the rear end, of waveguide 82. In addition, as shown, the front ends of both top ridge 90 and bottom ridge 91 are bevelled. Two holes 94 and 95, size 2-56, are provided in bottom ridge of 91 of waveguide 82 for receiving tuning screws 96 and 97, respectively, which are used to obtain a broader impedance match. Hole 94 is substantially coaxial with aperture 83. It is also noted that the rear screw 96 does not protrude into waveguide cavity 88, while front screw 97 does protrude into cavity 88.

Feed probe 84 is inserted into cavity 88 and is shorted to tuning screw 96, and thus to the bottom ridge 91 of waveguide 82 in order to control the VSWR of antenna 80. Preferably, probe 84 is oriented substantially perpendicularly with respect to bottom ridge 91. The diameter of probe 84 is reduced to approximately 0.5 mm to provide a better match to the high impedance ridges of waveguide 82. Antenna 80 further comprises a shorting plate 92 mounted at the rear of waveguide 82 and positioned with respect to feed probe 84 so as to obtain the smoothest impedance match over the operating bandwidth of the antenna. Shorting plate 92 is provided with a 2.2 mm diameter hole 93 to facilitate removal of air bubbles trapped in waveguide 82 when antenna 80 is immersed in the dielectric medium, and to permit alignment of antenna 80 with respect to the target. The dimension of hole 93 is determined by the bandwidth of the radiation to be transmitted, being sized so as to be below the cutoff frequency for the bandwidth of the radiation.

The dielectric of feed probe 84 is preferably inserted into aperture 83 such that the dielectric is approximately even with the upper interior surface of waveguide 82. Final impedance matching is obtained by simultaneous adjustment of tuning screws 96 and 97 and penetration of the dielectric into aperture 83.

Antenna 80 is advantageously enclosed in a conventional double ridged waveguide flange 99, which provides mechanical stability and means for mounting extensions onto antenna 80. Preferably, flange 99 is machined with notches 100 and 101 to permit connection of feed cable 86 onto connector 85, and access to tuning screws 96 and 97.

In use, antenna 80 and the associated flange 99 are advantageously mounted at the end of a hollow tube 102 which supports antenna 80 and provides a conduit which protects cable 86. Cable 86 is terminated at the distal end of tube 102 in a conventional type N connector 104. To reduce the effect of reflection off tube 102, antenna 80 is supported 5 cm in front of tube 102 by means of a metal standoff 106 and connector 107. Antenna 80 is designed to be operated totally immersed in the dielectric medium and have an operating bandwidth of 2000 MHF to 4000 MHF. The dimensions which have been cited hereinabove assume that the dielectric medium is water, which is preferably distilled and at a temperature of 32 C. If a medium with a different dielectric constant is to be used, then the dimensions would need to be altered accordingly. In general, if the medium has a dielectric constant lower than that of water, larger dimensions would be required, and conversely, if the medium has a dielectric constant higher than that of water, smaller dimensions would be required.

The various other components of system 10 can be conventional. For example, a Hewlett-Packard 8690B oscillator, Hewlett-Packard 8699 sweep generator, Microlab/FXR Model DA-2FN power divider, Watkins-Johnson Model M1G product detector, Krohn-Hite Model 3343 filter, and a Hewlett-Packard 5451B analyzer may be employed for oscillator 20, generator 22, power divider 30, product detector 40, filter 50, and analyzer 60, respectively.

It is also to be noted that system 10 may also advantageously include various well-known and conventional devices, such as attenuators, filters and the like which are commonly included in any microwave system to improve the operating characteristic thereof. Since such devices are not an aspect of the present invention, a detailed description thereof has been omitted in the interests of clarity.

Turning to the operation of system 10, when the time delay through test channel 32 and reference channel 34 is not the same, the instantaneous frequencies of the signals detected by detector 40 will be different, and the magnitude of the frequency difference will be inversely proportional to the sweep time $T_s$, and directly proportional to the difference in propagation times in the channels 32 and 34. Further, the amplitude of the direct path signal in channel 32 detected by detector 40 is a function of the attenuation through the target. More specifically, the general expression for the signal produced at the output of filter 50 resulting from a single ray path is as follows:

$$E = (\alpha\beta A^2/2)\cos[k_f T t - \omega_1 T - k_f T^2][U(t-T) - U(t-T_s)]$$

Where
$\omega_1 = 2\pi f_1$ = Start frequency (radians/second)
$\omega_2 = 2\pi f_2$ = Stop frequency (radians/second)
$T_s$ = Sweep time (seconds)
$T$ = Differential time delay between test and reference channels (seconds)
$t$ = Time (seconds)
$\alpha$ = Attenuation through the path under study β = Multiplier which is a function of the gain of the measurement system A = Amplitude of the signal at the power divider output $k_f = (\omega_2 - \omega_1)/T_s$ Radians/second$^2$ The function U(x) is defined as follows:
U(x)=0 for x<0
U(x)=1 for x≧0

The result, for a single path, is a truncated sinusoidal waveform with an angular frequency equal to $k_f T$ radians/second and with a phase offset equal to $(\omega_1 T + k_f T^2)$ radians.

If appropriate values for the above identified are chosen, such as for example:

$T_s$ = 7.75 milliseconds; $f_1$ = 2.0 GHz; and $f_2$ = 4.0 GHz; the $\omega_1 T$ term dominates the phase offset until the differential time delay T becomes very large (equivalent to a free space propagation distance of over 100 miles). Thus, for biologically relevant values of differential time delay, the time delay spectrum for a single path may be written as $$E = (\alpha\beta A^2/2) \cos [k_f Tt - \omega_1 T] [U(t-T) - U(t-T_s)]$$

For delays T less than the sweep time $T_s$, examination of the spectrum of the signal at the output of product detector 40 yields an unambiguous measure of time delay through the target. Furthermore, since time of propagation through a particular path in the target uniquely determines the frequency of a spectral line in the time delay spectrum, multiple paths can be resolved on the basis of time-of-arrival information.

Figure 3:
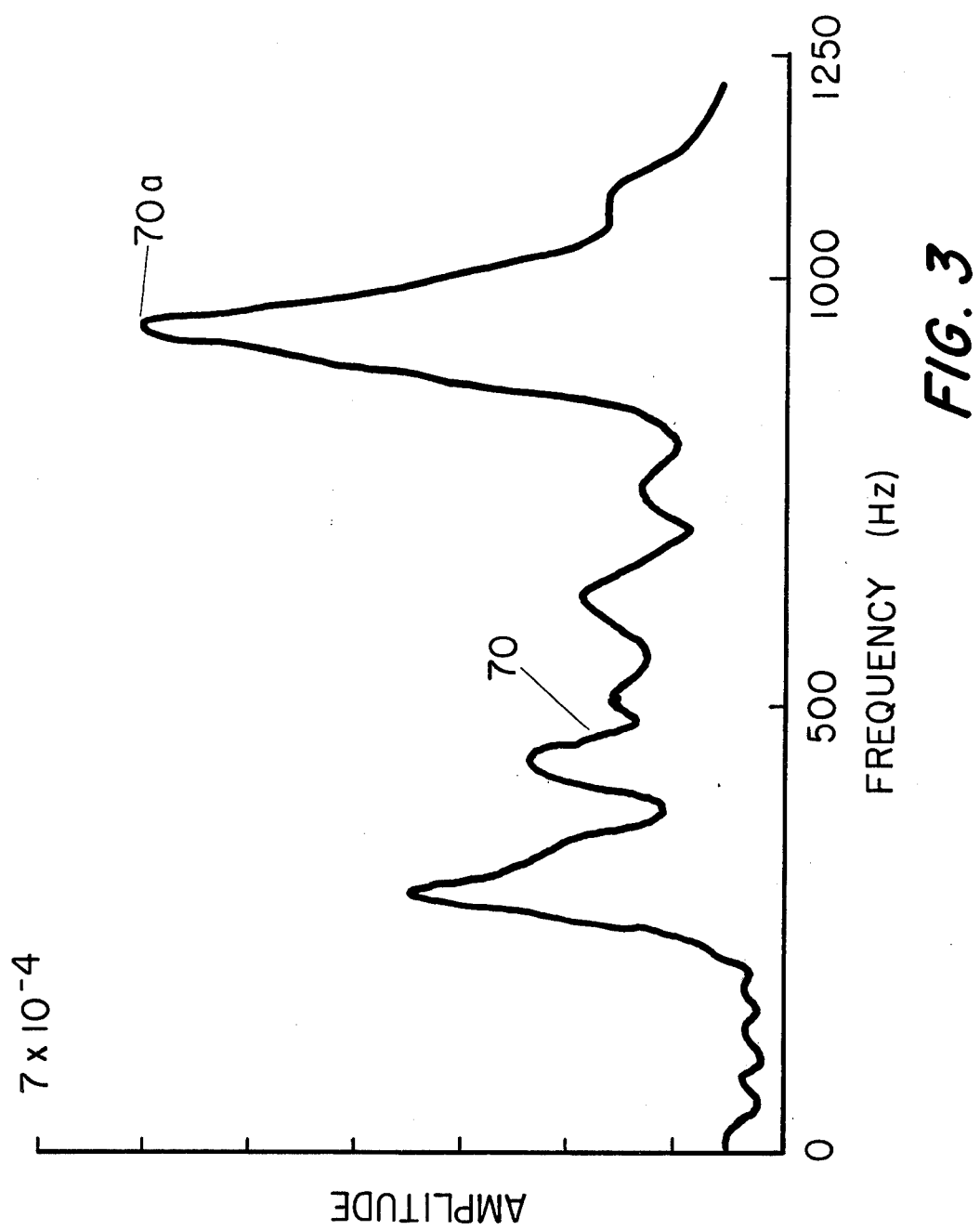
FIG. 3 is a graphical representation of an illustrative time delay spectrum produced by a system similar to that shown in FIG. 1 with an antenna of the type shown in FIGS. 2a–2b.

FIG. 3 illustrates a typical time delay spectrum produced at the output of filter 50 in a system 10 utilizing small apertured antennas 36 and 38 of the type illustrated in FIGS. 2a-2b. The waveform 70 constitutes the envelope of the individual spectral lines, which each represent the instantaneous difference in frequencies of the signals detected by detector 40, and thus represents the time delay for a particular path of propagation in test channel 32. The waveform 70 thus represents a composite time delay spectrum for all paths of propagation in test channel 32. The direct ray path through the target corresponds to the spectral line having the highest amplitude at the lowest frequency, e.g. point 70A on waveform 70 in FIG. 3. With antennas 36 and 38 of sufficiently small aperture, such as antennas of the type illustrated in FIGS. 2a-2b, the resolution of the direct ray path is readily accomplished since the time delay spectrum peaks sharply, as shown in FIG. 3, at the spectral line corresponding to the direct ray path. If the apertures of antennas 36 and 38 are not sufficiently small, resolution of the direct ray path is in principle still possible. However, additional analysis of the complex time delay spectrum which results is required, which becomes too involved to have practical utility, at least with respect to interrogation of biological targets, as the size of the antenna aperture increases. Once the system 10 is calibrated, as described in more detail hereinbelow, the time delay through the target may be determined directly from the frequency of the direct ray path spectral line. It is to be noted that the value of the time delay of the signal path provided by reference channel 34 may be chosen such that for a given biological target and environment, the output of product detector 40, and hence waveform 70, are in a frequency range, for example, the audio range, which is easily processed.

Figure 4:
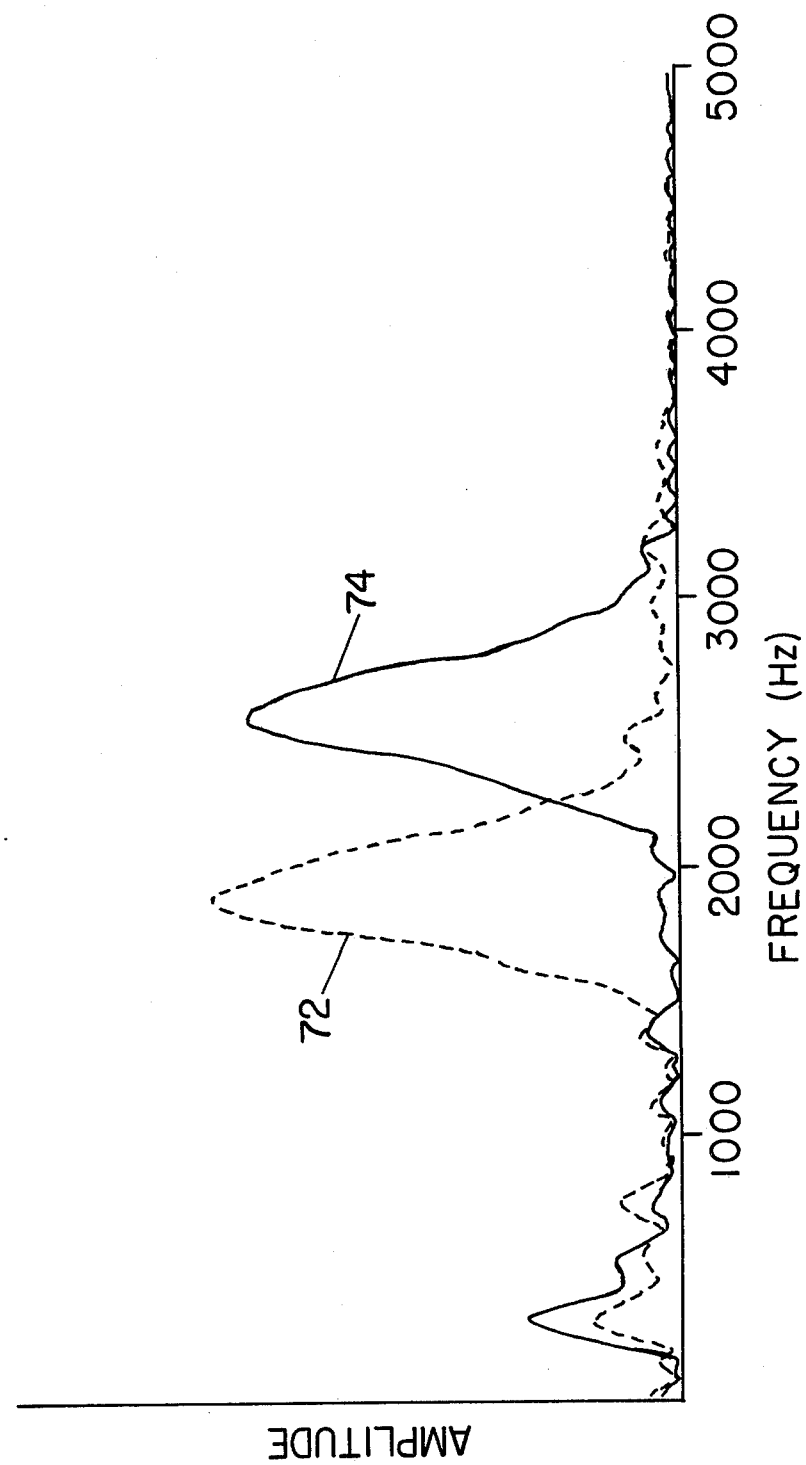
FIG. 4 is a graphical representation of the time delay spectrums produced by a system similar to that shown in FIG. 1 during calibration thereof.

System 10 is calibrated by determining the propagation delays caused by the elements of test channel 32 other than the target A. These delays may be either calculated therotetically, or determined empirically. Referring to FIG. 4, one method of empirically calibrating system 10 involves producing a time delay spectrum 72 with system 10 in its normal configuration. An element having a known time delay, e.g. a predetermined length of RG9/U coaxial cable, is inserted into test channel 32 between power divider 30 and antenna 36, and another time delay spectrum 74 is produced. The difference between the expected shift in the location of spectrum 74 with respect to spectrum 72, based on the time delay of the introduced element, and the actual shift which occurs provides a measure of the time delay introduced by the elements of test channel 32.

Tests conducted in connection with the preferred embodiment of the invention described hereinabove demonstrate that the measured data does not become ambiguous until the propagation time is equivalent to that of over 1400 miles in free space, which is manifestly adequate for biologically relevant targets. Additionally, the system is capable of discriminating between two ray paths whose differential time delay is on the order of 100 picoseconds, which corresponds to a differential path length of 6mm in brain tissue and the like.

Although the invention has been described with respect to an exemplary embodiment thereof, it will be understood that variations and modifications can be effected in the embodiment without departing from the scope or spirit of the invention.

We claim:

1. A method of microwave time delay spectroscopy for remote interrogation of a biological target comprising the steps of:

generating a microwave signal which varies in frequency from a first frequency to a second frequency in a predetermined time period;

dividing said signal into first and second propagation signals;

simultaneously propagating said first propagation signal through a test channel and said second propagation signal through a reference channel, said test channel comprising a transmitting antenna for transmitting said first propagation signal through the target, and a receiving antenna for receiving said first propagation signal transmitted through the target, and said reference channel providing a fixed time delay of propagation therethrough;

detecting and mixing said first and second propagation signals following said propagation thereof to produce a time delay spectrum wherein the frequency of each spectral line represents the instantaneous difference in frequencies of the detected signals.

2. The method of claim 1 and further comprising the step of:

analyzing the time delay spectrum to select the spectral line having the highest amplitude at the lowest frequency and thereby select the spectral line corresponding to the direct ray path through the target.

3. Microwave time delay spectroscopic apparatus for remote interrogation of a biological target, comprising means for generating a microwave signal which varies in frequency from a first frequency to a second frequency in a predetermined time period, means for dividing said signal into first and second propagation signals, a test channel through which said first propagation signal is propagated, said test channel comprising a transmitting antenna for transmitting said first propagation signal through the target, and a receiving antenna for receiving said first propagation signal transmitted through the target, a reference channel through which said second propagation signal is propagated, said reference channel providing a fixed time delay of propagation therethrough, means for detecting and mixing said first and second propagation signals following propagation thereof through said test and reference channels, respectively, to produce a time delay spectrum wherein the frequency of each spectral line represents the instantaneous difference in frequencies of the detected propagation signals.

4. The apparatus of claim 3 and further comprising means for analyzing said time delay spectrum to select the spectral line having the highest amplitude at the lowest frequency and thereby select the spectral line corresponding to the direct ray path through the target.

5. The apparatus of claim 4 wherein said microwave signal generating means comprises a swept microwave oscillator and sweep generator, said signal dividing means comprises a power divider, said detecting and mixing means comprises a product detector, and said analyzing means comprises a fourier analyzer.

6. The apparatus of claim 3 wherein said transmitting and receiving antennas and the target are immersed in a high dielectric medium.

7. The apparatus of claim 6 wherein said high dielectric medium is water.

* * * * *